United States Patent [19]
Köhler et al.

[11] Patent Number: 5,663,438
[45] Date of Patent: Sep. 2, 1997

[54] PREPARATION OF CYCLIC AMINES

[75] Inventors: Ulrich Köhler, Mannheim; Frank-Friedrich Pape, Kleinniedesheim; Matthias Irgang, Heidelberg; Joachim Wulff-Döring, Frankenthal; Michael Hesse, Schifferstadt; Peter Polanek, Weinheim, all of Germany

[73] Assignee: BASF Aktiengesellschaft, Ludwigshafen, Germany

[21] Appl. No.: 516,147

[22] Filed: Aug. 17, 1995

[30] Foreign Application Priority Data

Aug. 16, 1994 [DE] Germany ............... 44 29 014.4

[51] Int. Cl.$^6$ ............................................. C07C 209/68
[52] U.S. Cl. ..................... 564/305; 564/307; 564/402
[58] Field of Search .................. 564/305, 307, 564/402

[56] References Cited

U.S. PATENT DOCUMENTS

| | | | |
|---|---|---|---|
| 4,252,742 | 2/1981 | Blackwell et al. | 564/447 |
| 4,355,180 | 10/1982 | Goetz et al. | 564/402 |
| 4,376,645 | 3/1983 | Eicken et al. | 71/105 |
| 4,429,155 | 1/1984 | Göetz et al. | 564/402 |
| 5,072,044 | 12/1991 | Herkes | 564/305 |

FOREIGN PATENT DOCUMENTS

| | | |
|---|---|---|
| 22751 | 1/1981 | European Pat. Off. . |
| 53817 | 6/1982 | European Pat. Off. . |
| 53818 | 6/1982 | European Pat. Off. . |
| 53699 | 6/1982 | European Pat. Off. . |
| 167996 | 1/1986 | European Pat. Off. . |
| 3209148 | 9/1983 | Germany . |

*Primary Examiner*—Peter O'Sullivan
*Attorney, Agent, or Firm*—John J. Shurtleff

[57] ABSTRACT

A process for the preparation of a phenyl amine which may be substituted by alkyl or cycloalkyl in which the corresponding cyolohexylamine is reduced at temperatures of 150° to 300° C. and pressures of 0.01 to 50 bar in the presence of a heterogeneous dehydrogenation catalyst consisting essentially of palladium or a palladium/platinum mixture supported on carrier consisting of the oxides of rare earth metals and and metals of Group IVb of the Periodic Table of Elements, with the proviso that the palladium/platinum mixture may also be supported on an alumina carrier. The cyclohexylamine reactant can be advantageously prepared by reacting the corresponding phenol with ammonia and hydrogen at 100° to 250° C. in the presence of the same heterogeneous catalyst as a preliminary step to provide a two stage process using the same catalyst in both stages.

8 Claims, No Drawings

PREPARATION OF CYCLIC AMINES

The present invention relates to a process for the preparation of aromatic amines from aliphatic amines and their preparation by hydrogenation over noble metal catalysts under aminating conditions.

U.S. Pat. No. 5,072,044 discloses the dehydrogenation of cyclohexylamines to give the corresponding aromatic amines over Li-doped Pd catalysts. The reaction requires high reaction temperatures of from 360° to 380° C., which promote the formation of undesirable by-products.

The one-stage conversion of phenols with ammonia and hydrogen into cyclohexylamines in the presence of noble metal catalysts is disclosed, for example, in EP-A-22 751 and EP-A-53 819. Virtually exclusively the formation of the saturated cyclic amines is observed, whereas there is scarcely any formation of aromatic amines.

EP-A-167 996 describes the direct preparation of aromatic amines in a two-stage synthesis in a reactor having two reaction zones or in two reactors connected in series. Here, the hydrogenation to the cyclohexylamine under aminating conditions is carried out in the first stage at low temperatures (from 180° to 210° C.) and the dehydrogenation to the corresponding aromatic amine is carried out in the second stage, without prior working up, at higher temperatures (from 220° to 250° C.). A description of suitable catalysts is given, for example, in DE-A-32 09 148, EP-A-53 699, EP-A-53 817 or EP-A-53 818. During prolonged operation, however, it is found that the Pd catalyst which is used in the 2nd stage and contains 1% by weight of Pd on a carrier comprising 19.4% by weight of MgO and 80.6% by weight of $Al_2O_3$ is substantially more rapidly deactivated than the catalyst of the 1st stage, so that the plant has to be shut down frequently for catalyst change or catalyst regeneration.

It is an object of the present invention to remedy the above-mentioned disadvantages.

We have found that this object is achieved by a novel and improved process for the preparation of aromatic amines of the general formula I

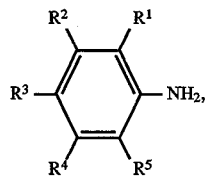

where $R^1$, $R^2$, $R^3$, $R^4$ and $R^5$ are each hydrogen, $C_1$–$C_{12}$-alkyl or $C_3$–$C_{12}$-cycloalkyl, from aliphatic amines of the general formula II

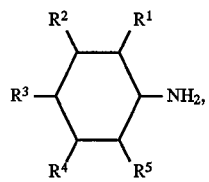

where $R^1$, $R^2$, $R^3$, $R^4$ and $R^5$ have the abovementioned meanings, at from 150° to 300° C. and from 0.01 to 50 bar in the presence of a heterogeneous catalyst, wherein the heterogeneous catalyst consists of from 30 to 100% by weight of
a) palladium on oxides of the rare earth elements and/or on oxides of subgroup IV or
b) platinum/palladium mixtures on alumina and/or oxides of the rare earth elements and/or oxides of subgroup IV and from 0 to 70% by weight of alkali metal and/or alkaline earth metal oxide, and the preparation of the aliphatic amines of the formula II by reacting phenols of the general formula III

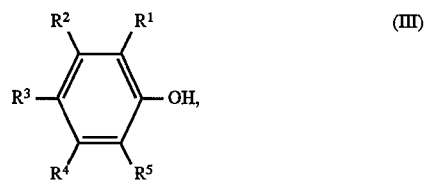

where $R^1$, $R^2$, $R^3$, $R^4$ and $R^5$ have the abovementioned meanings, with ammonia and hydrogen at from 100° to 250° C. and from 0.01 to 50 bar in the presence of an abovementioned catalyst.

The novel process can be carried out as follows:

The reaction of the aliphatic amines II to give the aromatic amines I can be carried out over a heterogeneous catalyst in the liquid phase, preferably in the gas phase, at from 150° to 300° C., preferably from 170° to 270° C., particularly preferably from 180° to 250° C., and from 0.01 to 50, preferably from 0.1 to 5, bar, particularly preferably at atmospheric pressure.

The reaction of the phenols III with ammonia and hydrogen to give the aliphatic amines II can be carried out over a heterogeneous catalyst in the liquid phase, preferably in the gas phase, at from 100° to 250° C., preferably from 120° to 220° C., particularly preferably from 140° to 200° C., and from 0.01 to 50, preferably from 0.1 to 5, bar, particularly preferably at atmospheric pressure.

Ammonia and hydrogen are used as a rule in a molar ratio of from 2:1 to 200:1, preferably from 3:1 to 100:1, particularly preferably from 4:1 to 40:1, based on the substituted phenol used. The molar ratio of ammonia to hydrogen may be from 100:1 to 0.01:1, preferably from 10:1 to 0.1:1, particularly preferably from 5:1 to 0.5:1.

The two reactions described above can be carried out in succession in two reaction zones, for example in a tube reactor.

However, all that is important in principle is to avoid back-mixing from the exit of the plant, i.e. the end of the last reaction zone, to the entrance, i.e. beginning of the first reaction zone, which can be most readily achieved in tube reactors and in the plug flow arising therein.

The catalyst can in each case be arranged in a fixed bed or in a fluidized bed. The novel heterogeneous catalysts prove to be tailor-made catalysts for the second reaction zone.

Suitable heterogeneous catalysts are those which consist of from 30 to 100%, preferably from 50 to 100, particularly preferably from 70 to 100,% by weight of
a) palladium on oxides of the rare earth elements and/or on oxides of subgroup IV or
b) platinum/palladium mixtures on alumina and/or oxides of the rare earth elements and/or oxides of subgroup IV and from 0 to 70, preferably from 0 to 50, particularly preferably from 0 to 30,% by weight of alkali metal and/or alkaline earth metal oxide.

Suitable oxides of the rare earth elements are those of the elements of the lanthanide and of the actinide group of the Periodic Table of Elements, such as cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium and lawrencium, preferably cerium, praseodymium, neodymium, samarium, europium, terbium, ytterbium, thorium and protactinium, particularly preferably cerium, praseodymim, neodymium and thorium.

Suitable oxides of subgroup IV, i.e., Group IVb of the Periodic Table of Elements, are those of titanium, zirconium and hafnium, preferably of titnium and zirconium, particularly preferably of zirconium.

Suitable alkali metal and/or alkaline earth metal oxides are those of lithium, sodium, potassium, rubidium, caesium, francium, beryllium, magnesium, calcium, strontium and barium, preferably of sodium, potassium, magnesium, calcium, strontium and barium, particularly preferably of sodium, potassium, magnesium, calcium and barium.

The active components of the catalyst (noble metals) are preferably present on oxides of the rare earth elements (lanthanides and actinides) or on oxides of subgroup IV in the case of pure palladium and preferably on carriers composed essentially of alumina, on oxides of the rare earth elements or on oxides of subgroup IV in the case of platinum/palladium.

The catalysts can be prepared either by kneading of the additives (in the form of the metal oxides) together with alumina, thermal aftertreatment (heating) at from 400° to 900° C. and impregnation with a solution containing the noble metal or by impregnation of the carrier with a solution of the additives and of the metal used for the hydrogenation, for example in the form of solutions of their nitrates, chlorides, formates, oxalates or ammoniates, and subsequent heating at from 400° to 900° C. In the case of the spinel formation, a temperature of from 900° to 1300° C. must be reached after the kneading or impregnation of the alumina with the oxide or with the solution of the added component (cf. Ullmanns Encyklopädie der technischen Chemie, 3rd edition (1955), Volume 6, pages 242 to 244, Gmelin, System No. 35, A1 Tl1934 to 1995, pages 26 to 28).

The noble metal content of the catalyst is as a rule from 0.0001 to 25, preferably from 0.001 to 20, particularly preferably from 0.05 to 15%, by weight, based on the carrier. The catalysts can be used, for example, in the form of moldings, e.g. extrudates, or as powder, depending on the intended use.

Compared with the known processes, the novel process has the advantage that, as a result of the use of active and more slowly deactivated catalysts in the dehydrogenation step, shutdowns for catalyst change during industrial operation are substantially minimized and the capacity is thus increased. Moreover, the catalysts developed have a higher initial selectivity with respect to the aromatic amine, so that the selectivity is correspondingly better over the entire life.

The formation of usually typical byproducts, such as cyclohexanols, dicyclohexylamines, diphenylamines, etc., can be substantially suppressed in this process so that only traces of these byproducts, if any at all, occur.

$R^1$, $R^2$, $R^3$, $R^4$ and $R^5$ in the compounds I, II and III have the following meanings:

hydrogen, $C_1$–$C_{12}$-alkyl, preferably $C_1$–$C_8$-alkyl, particularly preferably $C_1$–$C_4$-alkyl, such as methyl, ethyl, n-propyl, isopropyl, n-butyl, isobutyl, sec-butyl and tert-butyl, $C_3$–$C_{12}$-cycloalkyl, preferably $C_5$–$C_8$-cycloalkyl, particularly preferably $C_5$- or $C_6$-cycloalkyl, such as cyclopentyl or cyclohexyl.

All phenols III substituted by inert substituents can be used for the novel process, for example ortho-, meta- and para-cresol, ortho-ethylphenol, ortho-n-butylphenol, ortho-sec-butylphenol, 2,4-dimethylphenol, 2,6-dimethylphenol, 2,3,6-trimethylphenol, 2,4,6-trimethylphenol, 2-cyclohexylphenol, 2,6-dimethyl-3-cyclohexylphenol, 2,6-diethylphenol, 2,5-diisopropylphenol, 2-methyl-6-sec-butylphenol, 3-tert-butylphenol, 2,6-di-sec-butylphenol and 2,6-dicyclohexylphenol.

The compounds prepared by the process of the invention are used, for example, for the preparation of active ingredients in crop protection agents (DE-A-23 05 495, DE-A-26 48 008, DE-A-25 13 732 and DE-A-25 15 091).

EXAMPLES

Example 1 (comparative example)

8 kg of alumina are kneaded with 2 kg of magnesium oxide (in each case relative to pure $Al_2O_3$ and MgO) with the addition of about 10 liters of water and then extruded to give 4 mm extrudates. The extrudates obtained are dried at 120° C. for 6 hours and then heated at 450° C. for 2 hours.

The extrudates are impregnated in an impregnating drum with a palladium nitrate solution by spraying the 5% strength by weight solution at elevated temperatures onto the extrudates. Thereafter, the extrudates are dried at 120° C. for 4 hours and then calcined at 520° C. for 2 hours.

The catalyst A thus prepared (analogous to EP-A-167 996) contains 1% by weight of Pd on a carrier which consists of 19.4% by weight of magnesium oxide and 80.6% by weight of alumina.

750 ml of catalyst are introduced into an electrically heatable reactor tube having a capacity of 2.5 l and a length of 1 m. The reactor is then heated to 180° C. (5° C./min) in nitrogen (100 l/h) and kept at this temperature. 30 l/h of hydrogen are metered in during the next 4 hours. The nitrogen flow rate is then decreased over 4 hours until only hydrogen is passed through the reactor. The temperature is then increased initially to 200° C. and this temperature is maintained for 2 hours, after which it is increased to 220° C. and this temperature in turn is maintained for 2 hours. The activated catalyst is used directly for the experiment and is kept under nitrogen until the beginning of the experiment.

For the reaction, the mixture is brought to the reaction temperature at atmospheric pressure in an $NH_3$(90 l/h)/$H_2$ (210 l/h) stream. The temperature in the upstream evaporator is brought to the same value. 100 ml/h of feed are metered into the gas stream via the evaporator. After the reactor, the liquid reaction products are condensed by means of a two-stage high-efficiency condenser with a downstream cold trap and are analyzed by gas chromatography. After the end of the day of the experiment, flushing is continued for a further hour with ammonia/hydrogen and finally cooling is effected under nitrogen.

The feed for the experiments on the dehydrogenation step is prepared over several weeks in the apparatus at 180° C., analogously to EP-A-167 996. The dimethylcyclohexylamine prepared has the following composition:

| | | |
|---|---|---|
| 2.7% | of m-xylene | |
| 86.0% | of dimethylcyclohexylamine | (DMCHA) |
| 3.7% | of dimethylphenol | (DMP) |
| 7.3% | of dimethylaniline | (xylidene) |
| 4.9% | of water | (Karl Fischer titration) |

The feed is dehydrogenated over the activated catalyst day by day. After the end of the feed, the reactor is cooled in a stream of nitrogen and the catalyst is kept under nitrogen overnight. If the xylidene content falls below 60% (percent by area determined by GC), the reaction temperature is increased by 10° C. The results are shown in the table below.

| Duration [d] | Temp [8° C.] | Xylidene [%] | DMCHA/O [%] | m-Xylene [%] | DMP [%] |
|---|---|---|---|---|---|
| 2 | 220 | 74.6 | 21.2 | 3 | 0.1 |
| 8 | 230 | 62.6 | 33.4 | 2.8 | 0.4 |
| 12 | 240 | 61 | 3.4 | 3.3 | 0.9 |
| 15 | 250 | 61.7 | 30 | 3.9 | 11.5 |

The rapid deactivation of the catalyst is evident and must be compensated by frequently increasing the temperature.

Example 2

The procedure is similar to that in Example 1, except that catalyst B is used.

Catalyst B is prepared similarly to catalyst A, except that platinum nitrate is used instead of palladium nitrate. The catalyst thus prepared contains 1% by weight of Pt.

| Duration [d] | Temp [8° C.] | Xylidene [%] | DMCHA/O [%] | m-Xylene [%] | DMP [%] |
|---|---|---|---|---|---|
| 5 | 210 | 71 | 9.3 | 13.3 | 1.1 |
| 10 | 210 | 67 | 17.7 | 9.8 | 2.9 |
| 19 | 220 | 70.2 | 7.2 | 14.8 | 4.8 |
| 36 | 230 | 66.5 | 8.4 | 14.5 | 8 |

It is evident that this catalyst is deactivated substantially more slowly than catalyst A. However, it forms more m-xylene.

Example 3

The procedure is similar to that in Example 1, except that catalyst C is used. Catalyst C is prepared similarly to catalyst A except that a solution which contains equal amounts of palladium nitrate and platinum nitrate is used instead of the palladium nitrate solution. The catalyst thus prepared contains 0.5% by weight of Pt and 0.5% by weight of Pd.

| Duration [d] | Temp [8° C.] | Xylidene [%] | DMCHA/O [%] | m-Xylene [%] | DMP [%] |
|---|---|---|---|---|---|
| 3 | 210 | 71.4 | 21 | 5.1 | 1.1 |
| 10 | 210 | 64.1 | 28.4 | 5.1 | 1.2 |
| 20 | 220 | 76.6 | 13 | 7 | 2.2 |
| 40 | 220 | 71.8 | 21.6 | 4.4 | 1.1 |

It is evident that this catalyst is very slowly deactivated and also gives a low level of byproducts.

Example 4

The procedure is similar to that in Example 1, except that catalyst D is used.

6 kg of freshly precipitated cerium hydroxide are kneaded with 60 g of nitric acid and 120 g of water for 3 hours and then extruded to give 4 mm extrudates. The extrudates obtained are dried at 120° C. for 16 hours and then heated at 520° C. for 3 hours.

The extrudates are impregnated in an impregnating drum with a palladium nitrate solution by spraying 5% strength by weight solution at elevated temperatures onto the extrudates. Thereafter, the extrudates are dried at 120° C. for 4 hours and then calcined at 520° C. for 2 hours.

The catalyst thus prepared contains 1% by weight of Pd.

| Duration [d] | Temp [8° C.] | Xylidene [%] | DMCHA/O [%] | m-Xylene [%] | DMP [%] |
|---|---|---|---|---|---|
| 2 | 220 | 86.7 | 4.3 | 5.5 | 1.2 |
| 10 | 220 | 74.3 | 16 | 5.2 | 3 |
| 20 | 220 | 68.6 | 25.9 | 3.3 | 1.3 |
| 40 | 230 | 73 | 19.7 | 4 | 2.1 |

It is evident that this catalyst has a very high initial activity and is deactivated very slowly.

Example 5

The procedure is similar to that in Example 1, except that catalyst E is used. Catalyst E is prepared similarly to catalyst D, except that platinum nitrate is used instead of palladium nitrate. The catalyst thus prepared contains 1% by weight Pt.

| Duration [d] | Temp [8° C.] | Xylidene [%] | DMCHA/O [%] | m-Xylene [%] | DMP [%] |
|---|---|---|---|---|---|
| 4 | 210 | 64.3 | 17.9 | 7.8 | 0.8 |
| 10 | 210 | 62.1 | 24 | 5.7 | 0.7 |
| 14 | 220 | 71.8 | 12.5 | 10.4 | 0.7 |

It is evident that this catalyst is deactivated substantially more slowly than catalyst A. However, it forms more m-xylene.

Example 6

The procedure is similar to that in Example 1, except that catalyst F is used. Catalyst F is prepared similarly to catalyst A, except that $ZrO_2$ extrudates and, instead of the palladium nitrate solution, a solution which contains equal amounts of palladium nitrate and platinum nitrate are used. The catalyst thus prepared contains 0.5% by weight of Pt and 0.5% by weight of Pd.

| Duration [d] | Temp [8° C.] | Xylidene [%] | DMCHA/O [%] | m-Xylene [%] | DMP [%] |
|---|---|---|---|---|---|
| 3 | 210 | 72.4 | 19.6 | 5.2 | 0.1 |
| 8 | 210 | 70.7 | 23.0 | 4.4 | 0.1 |
| 10 | 210 | 68.8 | 25.0 | 4.2 | 0.1 |

It is evident that this catalyst has a high activity and is deactivated very slowly.

We claim:

1. A process for the preparation of aromatic amines of the formula I

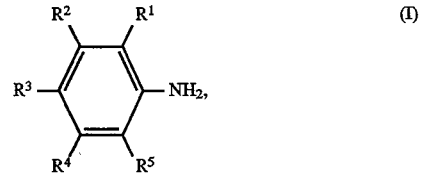

where $R^1$, $R^2$, $R^3$, $R^4$ and $R^5$ are each hydrogen, $C_1$–$C_{12}$-alkyl or $C_3$–$C_{12}$-cycloalkyl, from aliphatic amines of the formula II

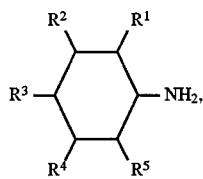

where $R^1$, $R^2$, $R^3$, $R^4$ and $R^5$ have the abovementioned meanings, at from 150° to 300° C. and from 0.01 to 50 bar in the presence of a heterogeneous catalyst, wherein the heterogeneous catalyst consists of from 30 to 100% by weight of a) palladium on oxides of the rare earth elements or on oxides of metals of Group IVb or b) platinum/palladium mixtures on alumina or oxides of the rare earth element or oxides of metals of Group IVb and from 0 to 70% by weight of alkali metal or alkaline earth metal oxide.

2. A process for the preparation of aromatic amines of the formula I as claimed in claim 1, wherein the aliphatic amines of the formula II are prepared by reacting phenols of the formula III

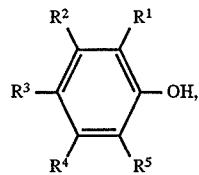

where $R^1$, $R^2$, $R^3$, $R^4$ and $R^5$ have the abovementioned meanings, with ammonia and hydrogen at from 100° to 250° C. and from 0.01 to 50 bar in the presence of a catalyst of claim 1.

3. A process for the preparation of aromatic amines of the formula I as claimed in claim 1, wherein a heterogeneous catalyst which consists of from 50 to 100% by weight of a) palladium on oxides of the rare earth elements or on oxides of metals of Group IVb or b) platinum/palladium mixtures on alumina or oxides of the rare earth elements or oxides of metals of Group IVb and from 0 to 50% by weight of alkali metal or alkaline earth metal oxide is used.

4. A process for the preparation of aromatic amines of the formula I as claimed in claim 1, wherein a heterogeneous catalyst which consists of from 70 to 100% by weight of a) palladium on oxides of the rare earth elements or on oxides of metals of Group IVb or b) platinum/palladium mixtures on alumina or oxides of the rare earth element or oxides of metals of Group IVb and from 0 to 30% by weight of alkali metal or alkaline earth metal oxide is used.

5. A process for the preparation of aromatic amines of the formula I as claimed in claim 1, wherein a heterogeneous catalyst which consists of from 30 to 100% by weight of $CeO_2$ as an oxide of the rare earth elements is used.

6. A process for the preparation of aromatic amines of the formula I as claimed in claim 1, wherein a heterogeneous catalyst which consists of from 30 to 100% by weight of $ZrO_2$ as an oxide of the rare earth elements is used.

7. A process for the preparation of aromatic amines of the formula I as claimed in claim 1, wherein $R^1$, $R^2$, $R^3$, $R^4$ and $R^5$ are each hydrogen, $C_1$–$C_8$-alkyl or $C_5$–$C_8$-cycloalkyl.

8. A process for the preparation of aromatic amines of the formula I as claimed in claim 1, wherein $R^1$, $R^2$, $R^3$, $R^4$ and $R^5$ are each hydrogen, $C_1$–$C_4$-alkyl or $C_5$- or $C_6$-cycloalkyl.

* * * * *